United States Patent
Poznansky et al.

(10) Patent No.: US 9,220,813 B2
(45) Date of Patent: *Dec. 29, 2015

(54) CELL THERAPY FOR LIMITING OVERZEALOUS INFLAMMATORY REACTIONS IN TISSUE HEALING

(75) Inventors: Mark C. Poznansky, Charlestown, MA (US); Nicolas A. F. Chronos, Atlanta, GA (US)

(73) Assignee: HOLY CROSS HOSPITAL, INC., Fort Lauderdale, FL (US)

( * ) Notice: Subject to any disclaimer, the term of this patent is extended or adjusted under 35 U.S.C. 154(b) by 558 days.

This patent is subject to a terminal disclaimer.

(21) Appl. No.: 13/031,431

(22) Filed: Feb. 21, 2011

(65) Prior Publication Data

US 2011/0178502 A1    Jul. 21, 2011

Related U.S. Application Data

(63) Continuation-in-part of application No. 12/729,653, filed on Mar. 23, 2010, now Pat. No. 8,603,463, which is a continuation of application No. 11/406,508, filed on Apr. 18, 2006, now Pat. No. 7,695,712.

(60) Provisional application No. 60/672,416, filed on Apr. 18, 2005.

(51) Int. Cl.
| | |
|---|---|
| C12N 5/0781 | (2010.01) |
| A61L 31/00 | (2006.01) |
| A61K 35/17 | (2015.01) |
| A61L 15/40 | (2006.01) |
| A61L 27/38 | (2006.01) |

(52) U.S. Cl.
CPC .............. *A61L 31/005* (2013.01); *A61K 35/17* (2013.01); *A61L 15/40* (2013.01); *A61L 27/3804* (2013.01); *A61L 27/3839* (2013.01)

(58) Field of Classification Search
None
See application file for complete search history.

(56) References Cited

U.S. PATENT DOCUMENTS

| | | | | |
|---|---|---|---|---|
| 5,213,960 | A | * | 5/1993 | Chang ................. 435/2 |
| 5,494,899 | A | * | 2/1996 | Kincade et al. ............. 514/10.2 |
| 5,777,084 | A | * | 7/1998 | Buhring ................... 530/388.22 |
| 5,840,502 | A | * | 11/1998 | Van Vlasselaer ........... 435/7.21 |
| 6,051,230 | A | | 4/2000 | Thorpe |
| 6,465,251 | B1 | * | 10/2002 | Schultze et al. ............. 435/377 |
| 6,753,135 | B2 | * | 6/2004 | Alters et al. ...................... 435/4 |
| 6,821,790 | B2 | * | 11/2004 | Mahant et al. ................ 436/177 |
| 7,695,712 | B2 | * | 4/2010 | Poznansky et al. ......... 424/93.7 |
| 2003/0003082 | A1 | | 1/2003 | Eisenbach-Schwartz |
| 2006/0210543 | A1 | | 9/2006 | Leor |
| 2006/0263339 | A1 | | 11/2006 | Poznansky |
| 2010/0015200 | A1 | | 1/2010 | McClain |
| 2010/0266561 | A1 | * | 10/2010 | Poznansky et al. ........ 424/93.71 |

FOREIGN PATENT DOCUMENTS

| | | |
|---|---|---|
| WO | 03044037 | 5/2003 |
| WO | 2004044584 | 5/2004 |

OTHER PUBLICATIONS

Boctor et al. "Cryoglobulinemia and cutaceous vasculitis". Transfusion (Malden), Feb. 2004, vol. 44, No. 2, p. 145.*
Klein et al. "Myocardial Protection by Na+—H+ Exchange Inhibition in Ischemic, Reperfused Porcine Hearts". Circulation. 1995; 92: 912-917.*
Burne-Taney, et al "B cell deficiency confers protection from renal ischemia reperfusion injury", J of Jmmunol, 171:3210-15 (2003).*
Burne-Taney, et al., Effects of combined T- and B-ceil deficiency on murine schemia reperfusion injury, Am. J Transpl 5:1186-93 (2005).*
Hoffman et al. Journal of Leukocyte Biology, 2003, vol. 74, p. 602-610.*
Zhang et al. PNAS, Mar. 2004, vol. 101. No. 11, pp. 3886-3891.*
Akashi, et al., "Blymphopoiesis in the thymus", J Immol., 164(10):5221-226 (2000).
Barbul, "Role of t-cell-dependent immune system in wound healing", Prog. Clin. Biol. Res., 266:161-75 (1988).
Bauer, et al., "Isolation of human B-cell subpopulations for pharmacological studies", Biotech. Progress, 7:391-6 (1991).
Boctor, et al., "Transfusion medicine illustrated. Cryoglobulinemia and cutaneous vasculitis", Transfusion, 44(2):145 (2004).
Burne-Taney, et al., "B cell deficiency confers protection from renal ischemia reperfusion injury", J of Immunol, 171:3210-15 (2003).
Burne-Taney, et al., "Effects of combined T- and B-cell deficiency on murine ischemia reperfusion injury", Am. J Transpl,, 5:1186-93 (2005).
Chang, et al., "Early fetal liver readily repopulates B lymphopoiesis in adult bone marrow", Stem Cells, 23(2):230-9 (2005).
Funderud, et al., "Functional properties of CD19-B lymphocytes positively selected from buffy coats by immunomagnetic separation", Eur. J Immunol., 20 (1):201-6 (1990).
Gulbins, et al., "Cell transplantation—A potential therapy for cardiac repair in the future", Heart Surg. Forum, 5(4):E-28-34 (2002).
Ikeda, et al., "Ischemic acute tubular models and drug discovery: a focus on cellular inflammation", Drug Disc Today, 11(7-8):364-70 (2006).
Kloner, et al., "Consequences of brief ischemia: Stunning preconditioning and their clinical implications: part 1", Cir, 104:2981-9 (2001).

(Continued)

*Primary Examiner* — Vera Afremova
(74) *Attorney, Agent, or Firm* — Buchanan Ingersoll & Rooney PC

(57) ABSTRACT

Cells of the B cell lineage including pre-pro-B cells, pro-B cells, pre-B cells, immature B cells, and some mature B cells, and/or cells of the T cell lineage, especially those with helper or regulatory function, most preferably autologous to the recipient, can be transplanted into damaged tissue to enhance recovery following injury. In a preferred embodiment, the cells are selected based on those cells which appear at the site of injury a few days after injury, such as macrophages, lymphocytes, which accelerate clean up and repair of the injured site and to mitigate the overzealous inflammatory response, presumably by inhibiting the inflammatory cells such as neutrophils and signals released thereby immediately following injury.

13 Claims, No Drawings

(56) References Cited

OTHER PUBLICATIONS

Kodituwakku, et al., "Isolation of antigen-specific B cells", Immunol Cell Biol, 81:163-70 (2003).

Monfalcone, et al., "increase leukocyte diversity and responsiveness to B-cell and T-cell mitogens in cell suspensions prepared by enzymatically dissociating murine lymph nodes", J Leukoc Biol., 39(6):617-28 (1986).

Niimi, et al., "Intrathymic administration of B cells induces prolonged survival of fully allogeneic cardiac grafts without prolonged deiection of donor-specific thymocytes", Transp Immunol, 6(3):177-81 (1998).

Oguchi, et al., "Myocardial ischemia and inflammation", Biomed Therapeutics, 37(2):31-34 (2003).

Witte, et al., "General principals of wound healing", Surg. Clin. N Am., 77:509-28 (1997).

BD Biosciences, Human and Mouse CD Marker Handbook (2010).

* cited by examiner

CELL THERAPY FOR LIMITING OVERZEALOUS INFLAMMATORY REACTIONS IN TISSUE HEALING

PRIOR RELATED APPLICATIONS

The present application is a continuation in part of U.S. Ser. No. 12/729,653 filed Mar. 23, 2010, which is a continuation of U.S. Ser. No. 11/406,508 filed Apr. 18, 2006, now U.S. Pat. No. 7,695,712, which claims the benefit of priority to U.S. provisional patent application Ser. No. 60/672,416 filed Apr. 18, 2005, all incorporated herein by reference in their entirety.

FIELD OF THE INVENTION

The present invention relates generally to methods of repairing tissue following injury through administration of relatively pure populations of B lymphocytes to the injured tissue.

BACKGROUND OF THE INVENTION

Loss of tissue function, whether by disease or accident, remains a major health problem. Heart and brain injuries, for example, are two of the leading causes of death and disability throughout the world. In the United States, cardiac disease accounts for 40% of all deaths and is the leading cause of congestive heart failure (American Heart Association. Heart and Stroke Update. Dallas, Tex.: American Heart Association; 2003). Cardiac disease that leads to acute myocardial infarction or chronic myocardial ischemia can also cause significant degradation in cardiac function. If the ischemic episode is limited in severity or duration, then cardiomyocytes survive and are protected from further ischemic insult through several preconditioning mechanisms. However, with acute and prolonged severe periods of ischemia, cardiomyocyte death occurs (Kloner R A, et al., Consequences of brief ischemia: stunning, preconditioning, and their clinical implications: part 1. Circ. 2001; 104:2981-2989). Under normal conditions, adult human cardiomyocytes lack the capability to regenerate, and over time, damaged myocardial cells are replaced by connective scar tissue along with a compensatory hypertrophy of the remaining viable cardiomyocytes (Gulbins H, et al., Heart Surg Forum 2002; 5(4):E28-34). This replacement of infarct by scar tissue leads to a loss of functional myocardium within the ischemic area, a progressive remodeling of the non-ischemic area, or border zone, and an overall reduction in cardiac performance.

Stroke is the third leading cause of death in the United States and the number one cause of adult disability. Ischemic stroke caused by blood flow interruption to the brain due to blockage of an artery by a blood clot accounts for about 70-80 percent of all strokes. A loss of blood flow to the brain deprives an area of brain cells of oxygen and nutrients which results in cell death. Body functions controlled by the area of the brain that has been damaged are lost. These functions include speech, movement and memory.

Repair of injured tissue is a complex process that begins at the moment of injury and can continue for months to years. This process can be broken down into three major phases; inflammatory, proliferative and remodeling. (Witte M B, et al. Surg Clin North Am 1997, 77:509-528). The inflammatory phase is immediate and can last for 5 to 7 days. During this phase, if there is tissue damage and/or cellular disruption as with trauma, vasoconstriction occurs and a clot forms which serves as a temporary protective shield for the exposed or damaged tissues. The clot provides cytokines and growth factors released by activated platelets that initiate the wound closure process and chemotactic signals to recruit circulating inflammatory cells to the wound site. Vasodilation follows and phagocytosis is initiated. The proliferative phase is next and can last up to three weeks. During this phase granulation commences and involves the formation of a bed of collagen by fibroblasts which results in the filling of the defect. New capillaries are formed in a process called granulation tissue formation, which is followed by contraction in which the wound edges come together to reduce the lesion. The last stage of the proliferative phase is re-epithelialization. In skin wound healing, keratinocytes move in all directions from a point of origin across a provisional matrix to cover the wound. The final phase of tissue repair is the remodeling phase. It can last up to two years and includes the production of new collagen which continues to increase the tensile strength of the wound.

The immune system has been recognized as an important regulator of tissue repair. It is composed of two parts, humoral and cellular defenses. The humoral arm includes antibodies and complement. The cellular arm includes neutrophils, macrophages and T lymphocytes. These cell populations migrate into the wound in an ordered timeframe and contribute to the repair process through the secretion of signaling molecules in the forms of cytokines, lymphokines and growth factors. (Witte M B, et al., Surg Clin North Am 1997, 77:509-528). Neutrophils are the first cells to appear at the wound site and are responsible for phagocytosis and debridement. Macrophages are the next cells to migrate into the wound. They complete the inflammatory and debridement processes and deliver critical tissue repair cytokines and growth factors. T lymphocytes are the last cells to migrate into the lesion and appear during the proliferative phase. Their role includes the downregulation of the inflammatory response and growth state as this phase of the process concludes (Barbul A., Prog Clin Biol Res 1988, 266:161-175).

The role of B cells (B lymphocytes) in tissue repair, for example, is unclear and is presumed by those knowledgeable in the field to be inconsequential since helper T2 cell cytokines and B lymphocyte activating factors have not been detected at the wound site. What little evidence exists on the role of B cells in tissue repair suggests B cells have a pathogenic role (Zhang M, et al., Proc Natl Acad Sci USA 2004, 101:3886-3891).

Instead, B cells are best known for the role they play in the production of antibodies. They are generated from hematopoietic stem cells (HSCs) throughout life, first in the fetal liver and then in the adult bone marrow. Cytoplasmic cascades are initiated in response to tissue microenvironment signals that result in altered expression of proteins required for B cell maturation. The mature bone marrow B cell expresses IgD on its surface membrane which protects it from self antigen induced death. This mature cell moves into the periphery where it can be activated by antigen to become either an antibody-secreting plasma cell or a memory B cell.

While treatment options available to patients who have lost tissue function have increased recently, these options remain limited in their effectiveness. New therapies that can limit the amount of cell death and restore loss of body function are greatly needed. Evidence of cells engrafting into the damaged tissue coupled with an improvement of function supports this approach. While many groups are eager to begin treating patients with various cells, researchers are just now beginning to understand some of the mechanisms of how these cells repair injured tissue. What is needed is an identification of which cell, or combination of cells, is most appropriate for the repair of damaged tissue.

While many different cell therapy methods are being tried, the common goal in cell therapy is the introduction into injured tissue of a cell that is either functionally related to the targeted tissue, such as with delivery of skeletal myoblasts into damaged myocardium, or primordial cells (stem or progenitor cells) that are hoped will regenerate new tissue and structures thereby returning function to the injured organ. The bone marrow is a well understood source of stem cells for a variety of tissue but primarily for the blood system. Early attention was given to the bone marrow as a source of potentially therapeutic cells after several studies demonstrated that animals with labeled bone marrow cells that were subjected to a tissue injury such as a myocardial infarction were found to have some of these labeled bone marrow cells integrated into the healing tissue. However, while integration of bone marrow derived cells into healed tissue was demonstrated, many questions remain unanswered including what cell type from the bone marrow integrated into the tissue and the extent to which these cells contributed to the functional recovery of the injured tissue. Experimentation into bone marrow derived cell therapy has utilized either the entire bone marrow, also known as unfractionated bone marrow, or the isolation of the endothelial progenitor, hematopoietic (CD34+, AC133+) and nonhematopoietic (CDstro1+) stem cells contained within it. While the experimental use of unfractionated bone marrow, bone marrow derived progenitor, and stem cells continues, early results from their use have been disappointing due to only modest improvement or negative outcomes, questioning the relevance of the earlier animal experimentation and the therapeutic value of bone marrow derived cells.

It is therefore an object of the present to provide characterized cell populations for tissue repair.

It is a further object of the present invention to provide cell populations for tissue repair that do not persist at the site of repair, either in their original form or in some sort of differentiated form.

SUMMARY OF THE INVENTION

Cells of the B cell lineage including pre-pro-B cells, pro-B cells, pre-B cells, immature B cells, and some mature B cells, and/or cells of the T cell lineage, especially those with helper or regulatory function, most preferably autologous to the recipient, can be transplanted into damaged tissue to enhance recovery following injury. One of the benefits of using these cells is that the cells do not persist in the tissue in which they are administered, serving only to enhance repair, not create tissue or permanently alter the endogenous cell types. In a preferred embodiment, the cells are selected based on those cells which appear at the site of injury a few days after injury, such as macrophages, lymphocytes, B and T cells, then are administered at the time of injury. Most preferably the cells do not include stem cells or other types of partially differentiated cells such as mesenchymal cells, but are terminally differentiated cells. These cells appear to accelerate clean up and repair of the injured site. They also appear to mitigate the overzealous inflammatory response, presumably by inhibiting the inflammatory cells such as neutrophils and signals released thereby immediately following injury.

The cells may be administered locally or systemically. Cells administered systemically via the blood stream tend to go to injured tissue. Targeting may be enhanced by attaching homing signals to increase specificity of delivery. Examples of useful targeting signals include glycoproteins. Cells can also be primed by initially culturing under anoxic conditions or using biological or chemical inducers, or are otherwise altered by exposure to varying chemical or physical conditions such as temperature, pressure, osmotic conditions, pH, and varying concentrations of molecular compounds, electrolytes, and proteins such as B cell activating factor, and similar agents.

In the preferred applications, the cells are administered to individuals with damage due to ischemia, before, during or after surgery to limit metastasis, prior to, during or after placement of an implant such as a stent to limit restenosis, and after injury but prior to healing to limit excessive proliferation of tissue that may cause scarring.

DETAILED DESCRIPTION OF THE INVENTION

It has been discovered that T and B cells, preferably terminally differentiated cells not including stem cells or other pluri- or multi-potent cells, can be administered to an individual to aid in tissue repair.

I. Cell Compositions

The cells are preferably B and/or T cells. The cells to be administered are preferably autologous cells and are harvested from the donor using techniques known to one of ordinary skill in the art. Sources of such B cells are generally known and include, but are not limited to, bone marrow, blood, spleen, lymph nodes, and allogeneic sources. The cells are then purified from the heterogeneous cell population in order to obtain a relatively pure population of cells. Such purification techniques are described in the present application. Kits are provided to purify B cells from the heterogeneous cell populations. Preferred cells are autologous.

A. B Cells

Preferred cell types to be administered to injured tissue are beta (B) lymphocytes and/or precursors thereof, hereinafter called a B cell or B lymphocyte. Any type of B cell may be used. B cells can be characterized by the presence of specific surface proteins, as known to one of ordinary skill in the art. These include, but are not limited to, B220, CD19, CD43, CD45RA, CD5, Mac-1, IgM, IgD, IgG, CD62L, CD23, CD21, CD40 and B cell receptor ($Ig_{\alpha\beta}$). In one embodiment the B cells are human B cells and are characterized by having one or more CD19, B220 or B cell receptor ($Ig_{\alpha\beta}$) surface proteins.

In one embodiment, the B cells used for treating injured tissue should be relatively pure and should not contain appreciable numbers of stem cells. As used herein, relatively pure means at least 80% pure, 85% pure, 88% pure, or even higher degrees of purity such as at least 90% pure, preferably at least 95% pure, preferably at least 97% pure, or preferably at least 98% pure as determined by fluorescence activated cell scan (FACS) analysis. The B cell population in the bone marrow is heterogeneous, containing pre-pro-B cells, pro-B cells, pre-B cells, immature B cells, and some mature B cells. All or some of these different types of B cells can be used.

Any source of B cells may be used. Such B cells may be derived from the bone marrow, spleen, lymph nodes, blood or other allogeneic tissues that are sources of B cells, as known to one of ordinary skill in the art. Preferred sources of B cells are bone marrow and blood. References for such methods include: Funderud S, et al., Functional properties of CD19+B lymphocytes positively selected from buffy coats by immunomagnetic separation. Eur J Immunol 1990 20(1):201-6; Monfalcone et al., Increase leukocyte diversity and responsiveness to B-cell and T-cell mitogens in cell suspensions prepared by enzymatically dissociating murine lymph nodes. J Leukoc Biol 1986 39(6):617-28; and, Miltenyi Biotec sells kits with protocols to isolate B cells and plasma cells from tissue.

Using sterile techniques known to one of ordinary skill in the art, in one embodiment, bone marrow is preferably obtained from the posterior superior ilium. The B cells may be immediately used after isolation and relative purification, may be stored for subsequent use, or may be cultured for a period of time before use. The B cell population in the bone marrow contains pre-pro-B cells, pro-B cells, pre-B cells, immature B cells, and some mature B cells. In the present application, the term B cell encompasses pre-pro-B cells, pro-B cells, pre-B cells, immature B cells, and mature B cells. B cells can be isolated using techniques known to one of ordinary skill in the art from blood or other tissues.

Methods to obtain B cells or precursor B cells from heterogeneous cell populations are known to one of ordinary skill in the art. Many of these techniques employ primary antibodies that recognize molecules on the surface of the desired B cells or B cell precursors and use these antibodies to positively select these cells and separate them from unwanted cells. This technique is known as positive selection. Other techniques commonly employed by one of ordinary skill in the art use primary antibodies that recognize molecules on the surface of the cells to be separated from the desired B cells or B cell precursors. In this manner, molecules on these unwanted cells are bound to these antisera and these cells are removed from the heterogeneous cell population. This technique is known as negative selection. A combination of positive and negative selection techniques may be employed to obtain relatively pure populations of B cells or precursor B cells. As used herein, relatively pure means at least 80% pure, 85% pure, 88% pure, or higher degrees of purity such as at least 90% pure, at least 95% pure, at least 97% pure, or at least 98% pure.

Numerous techniques are available to one of ordinary skill to separate antibodies bound to cells. Antibodies may be linked to various molecules that provide a label or tag that facilitates separation. In one embodiment, primary antibodies may be linked to magnetic beads that permit separation in a magnetic field. In another embodiment, primary antibodies may be linked to fluorescent molecules that permit separation in a fluorescent activated cell sorter. Fluorescent and magnetic labels are commonly used on primary and/or secondary antibodies to achieve separation. Secondary antibodies which bind to primary antibodies may be labeled with fluorescent molecules that permit separation of cells in a fluorescence activated cell sorter. Alternatively, metallic microbeads may be linked to primary or secondary antibodies. In this manner, magnets may be used to isolate these antibodies and the cells bound to them.

To achieve positive or negative selection, the heterogeneous cell population is incubated with primary antibodies for a time sufficient to achieve binding of the antibodies to the antigen on the cell surface. If the primary antibodies are labeled, separation may occur at this step. If secondary antibodies are employed, then the secondary (anti-primary) antibodies are incubated with the cells bound to the primary antibodies for a time sufficient to achieve binding of the secondary antibodies to the primary antibodies. If the secondary antibody has a fluorescent label, then the cells are sent through a fluorescence activated cell sorter to isolate the labeled antisera bound to the desired cell. If the secondary antibody has a magnetic label, then the selected cell with the primary antibody and secondary antibody-labeled microbeads form a complex that when passed through a magnet remain behind while the other unlabeled cells are removed along with the cell medium. The positively labeled cells are then eluted and are ready for further processing. Negative selection is the collection of the unlabeled cells that have passed through the magnetic field.

MACS Technology (Miltenyi Biotec) is based on the use of MACS MicroBeads, MACS Columns and MACS Separators. This technology is known to one of ordinary skill in the art. MACS MicroBeads are superparamagnetic particles that are coupled to highly specific monoclonal antibodies. They are used to magnetically label the target cell population. They are approximately 50 nm in size, not visible with light microscopy, biodegradable, and gentle on cells. As the MicroBeads are extremely small, the use of a high-gradient magnetic field is required to retain the labeled cells. The MACS Column Technology is specifically designed to generate this strong magnetic field while maintaining optimal cell viability and function. By using a MACS Column with a coated, cell-friendly matrix placed in a permanent magnet, the MACS Separator, the magnetic force is now sufficient to retain the target cells labeled with a minimum of MicroBeads. By simply rinsing the column with buffer, all the unlabeled cells are washed out thoroughly, without affecting the labeled or unlabeled cell fractions, thus ensuring optimal recovery. By removing the column from the magnet, the labeled fraction can be obtained. With MACS Technology both the labeled and the unlabeled fraction are now highly pure, and an optimal recovery of the cells is guaranteed.

Isolation of B cells from heterogeneous cell populations and stem cell populations involves the negative selection process in which the marrow first undergoes red cell lysis by placing the bone marrow in a hypotonic buffer and centrifuging the red blood cells out of the buffer. The red blood cell debris remains in the supernatant which is removed from the test-tube. The bone marrow derived cells are then resuspended in a buffer that has the appropriate conditions for binding antibody. Alternatively, the bone marrow can be subjected to a density gradient centrifugation. The buffy coat layer containing the bone marrow derived cells is removed from the gradient following the centrifugation. The cells are washed and resuspended in the antibody binding buffer and is then incubated with primary antibodies directed toward stem cells, T cells, granulocytes and monocytes/macrophages (called lineage depletion) followed by positive selection using antibodies toward B cells.

In a preferred embodiment, anti-CD3 and anti-CD4 antibodies are used for T cells, anti-CD11b/c antibodies are used for monocytes/macrophages, anti-granulocyte antibodies are used for granulocytes, c-kit antibodies are used for stem cells, and CD45RA antibodies are used for rat B cells.

In another embodiment, the primary antibodies are attached to a matrix and the cells are incubated with this matrix. Those cells with surface antigens recognized by the primary antibodies are bound to the primary antibodies while other cells without these surface antigens are not. In one embodiment, this matrix is contained in a syringe and acts as an affinity column. Bound cells are subsequently eluted from the column and may be used at this stage or subjected to a further purification step in another affinity column containing the same primary antibody or another primary antibody that recognizes another surface antigen on the target cell. Elution of bound cells may occur using techniques such as adjustment of pH, addition of a buffer of altered tonicity, salt or other techniques useful for interfering with antigen-antibody binding known to one of ordinary skill in the art. These affinity columns may be used for positive selection, negative selection or both, in order to obtain a relatively pure preparation of B cells for administration to the injured tissue.

B cells may be optionally pretreated by exposing them to hypoxic conditions in order to increase B cell adhesion to mesenchymal cells and to enhance B cell activity. This pretreatment can be achieved once the bone marrow is harvested and the B cells isolated as described earlier. Prior to delivery of the B cells, the B cells are incubated within a closed system containing a sub-physiologic level of oxygen.

B. T Cells

T cells or T lymphocytes play a central role in cell-mediated immunity. They can be distinguished from other lymphocyte types, such as B cells and natural killer cells (NK cells) by the presence on their cell surface of T cell receptors (TCR). Several different subsets of T cells have been discovered, each with a distinct function.

T helper cell ($T_H$ cells) assist other white blood cells in immunologic processes, including maturation of B cells into plasma cells and activation of cytotoxic T cells and macrophages, among other functions. These cells are also known as $CD4^+$ T cells because they express the CD4 protein on their surface. Helper T cells become activated when they are presented with peptide antigens by MHC class II molecules that are expressed on the surface of Antigen Presenting Cells (APCs). Once activated, they divide rapidly and secrete small proteins called cytokines that regulate or assist in the active immune response. These cells can differentiate into one of several subtypes, including $T_H1$, $T_H2$, $T_H3$, $T_H17$, or $T_{FH}$, which secrete different cytokines to facilitate a different type of immune response. The mechanism by which T cells are directed into a particular subtype is poorly understood, though signalling patterns from the APC are thought to play an important role.

Cytotoxic T cells ($T_C$ cells, or CTLs) destroy virally infected cells and tumor cells, and are also implicated in transplant rejection. These cells are also known as $CD8^+$ T cells since they express the CD8 glycoprotein at their surface. These cells recognize their targets by binding to antigen associated with MHC class I, which is present on the surface of nearly every cell of the body. Through IL-10, adenosine and other molecules secreted by regulatory T cells, the $CD8^+$ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise two subtypes: central memory T cells ($T_{CM}$ cells) and effector memory T cells ($T_{EM}$ cells). Memory cells may be either $CD4^+$ or $CD8^+$ Memory T cells typically express the cell surface protein CD45RO.

Regulatory T cells ($T_{reg}$ cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus. Two major classes of CD4 regulatory T cells have been described, including the naturally occurring $T_{reg}$ cells and the adaptive $T_{reg}$ cells. Naturally occurring $T_{reg}$ cells (also known as $CD4^+$ $CD25^+$ $FoxP3^+$ $T_{reg}$ cells) arise in the thymus, whereas the adaptive $T_{reg}$ cells (also known as Tr1 cells or Th3 cells) may originate during a normal immune response. Naturally occurring $T_{reg}$ cells can be distinguished from other T cells by the presence of an intracellular molecule called FoxP3. Mutations of the FOXP3 gene can prevent regulatory T cell development, causing the fatal autoimmune disease IPEX.

Natural killer T cells (NKT cells) are a kind of lymphocyte that bridges the adaptive immune system with the innate immune system. Unlike conventional T cells that recognize peptide antigen presented by major histocompatibility complex (MHC) molecules, NKT cells recognize glycolipid antigen presented by a molecule called CD1d. Once activated, these cells can perform functions ascribed to both $T_h$ and $T_c$ cells (i.e., cytokine production and release of cytolytic/cell killing molecules). They are also able to recognize and eliminate some tumor cells and cells infected with herpes viruses. Vitamin D works with "naive" T-cells and activates them so they can attack foreign pathogens. When a T-cell encounters a foreign pathogen like an invading virus or harmful bacteria, the first thing that it does is look around for vitamin D. Once the T-cell finds vitamin D, it binds to it to "activate" itself and become a killer T-cell. Without this activation, T-cells may detect the pathogen, but will not respond with an attack and instead remain "naive". In this way vitamin D acts as the "on" switch for T-cells.

Activation of CD4+ T cells occurs through the engagement of both the T cell receptor and CD28 on the T cell by the Major histocompatibility complex peptide and B7 family members on the APC, respectively. Both are required for production of an effective immune response; in the absence of CD28 co-stimulation, T-cell receptor signalling alone results in anergy.

The various types of T cells may be isolated using the same techniques and means as for B cells, substituting the appropriate T cell specific antibodies.

C. Phagocytic Cells

In some cases, it may be advantageous to include phagocytic cells such as macrophages or monocytes.

Monocytes are produced by the bone marrow from haematopoietic stem cell precursors. Monocytes circulate in the bloodstream for about one to three days and then typically move into tissues throughout the body. They constitute between three to eight percent of the leukocytes in the blood. Half of them are stored as a reserve in the spleen. In the tissues monocytes mature into different types of macrophages at different anatomical locations.

Monocytes which migrate from the bloodstream to other tissues will differentiate into tissue resident macrophages or dendritic cells. Monocytes and their macrophage and dendritic cell progeny serve three main functions in the immune system: phagocytosis, antigen presentation and cytokine production. Phagocytosis is the process of uptake of microbes and particles followed by digestion and destruction of this material. Monocytes can perform phagocytosis using intermediary proteins such as antibodies or complement that coat the pathogen, as well as by binding to the microbe directly via pattern-recognition receptors that recognize pathogens. Monocytes are also capable of killing infected host cells via antibody, termed antibody-mediated cellular cytotoxicity.

Monocytes replenish resident macrophages and dendritic cells under normal states, and in response to inflammation signals, can move quickly, approximately 8-12 hours, to sites of infection in the tissues and divide/differentiate into macrophages and dendritic cells to elicit an immune response.

Macrophages can be identified by specific expression of a number of proteins including CD14, CD11b, F4/80 (mice)/ EMR1 (human), Lysozyme M, MAC-1/MAC-3 and CD68 by flow cytometry or immunohistochemical staining One important role of the macrophage is the removal of necrotic cellular debris in the lungs. Removing dead cell material is important in chronic inflammation, as the early stages of inflammation are dominated by neutrophil granulocytes, which are ingested by macrophages if they come of age. The removal of necrotic tissue is, to a greater extent, handled by fixed macrophages, which will stay at strategic locations such as the lungs, liver, neural tissue, bone, spleen and connective tissue, ingesting foreign materials such as pathogens, recruiting additional macrophages if needed. When a macrophage ingests a pathogen, the pathogen becomes trapped in a phagosome, which then fuses with a lysosome.

D. Kits

1. Kits for Isolation and Purification

Kits may be used to prepare relatively pure populations of B cells that may be used subsequently for administration to ischemic tissue. Such kits include various antibodies known to one of ordinary skill in the art that are useful in selecting and separating desired cells from a heterogeneous population of cells. These antibodies generally comprise primary antibodies that recognize surface antigens, such as proteins, polypeptides and glycoproteins that are characteristic of specific cells and are known to one of ordinary skill in the art. These kits may include such antibodies that recognize these surface antigens. Directions for using a kit are enclosed with each kit.

These kits may include materials and apparatus used in harvesting B and/or T cells. For example, if the B cell is obtained from bone marrow, these kits may include an 11 gauge tapered needle device designed to penetrate into the interior of bone usually the posterior superior ilium but sometimes the sternum, iliac crest, tibia or femur. Once penetrated, a polycarbonate syringe is attached and a vacuum applied to obtain the marrow. The kits include antibodies and materials that are specific for the cell type to be isolated, for example B cells, and may be further specialized for use in the heterogeneous cell mixture obtained from a specific tissue or organ. Materials may include apparatus or reagents useful in separation or preparation such as tubing conduits, separators, filtrators, and containers, incubation apparatus including tissue culture equipment and containers, and chemical or molecular reagents. Iisolation of B cells from a cell preparation from bone marrow may require the use of an antibody or antibodies specific for the surface antigens on the bone marrow derived B cells.

A kit may include an antibody or antibodies specific for the surface antigens on the bone marrow derived cells to be separated from the desired bone marrow derived B cells. A positive selection technique may be used optionally in combination with a negative selection technique. In order to facilitate negative selection, kits may be designed to include antibodies that are specific for all cell types except for the type to be isolated, for example B cells, in order to isolate the cell type through negative selection. The tools contained in these kits may be constructed of materials such as plastics, stainless steel, nitinol, rubber and other materials that bind, concentrate or exclude cells. The kits may also contain primary antibodies that are labeled so that the labeled cells may be separated by techniques know to one of ordinary skill, including, but not limited to, immunomagnetic separation. Such labels are commercially available. These kits may optionally contain secondary antibodies, which themselves may be labeled, and which may bind to the primary antibodies. Labels that may be attached to antibodies are known to one of ordinary skill in the art and include, but are not limited to, light emitting labels and magnetically responsive labels. Antibodies may be stored in containers in the kits which may be customized for protection from light, heat or other undesirable conditions. Antibodies may be stored in a lyophilized state or in a convenient buffer system optionally containing a preservative. Kits may also contain pharmaceutically acceptable buffers for use in handling samples during purification and elution steps, and for suspension of the isolated B cells for storage or for subsequent administration to the cell donor.

In one embodiment, kits may contain antibodies for positive selection, negative selection or both, in the form of affinity columns. Such columns may contain antibodies bound at their Fc region to a matrix within the columns. Heterogeneous cell preparations may be introduced into the affinity column.

These kits may also contain containers for mixing the antibodies with the cell preparations, means to transfer solutions such as pipetting means, graduated flasks, graduated centrifuge tubes, and the like. Further, the kits may include prepackaged closed systems to insure sterility.

2. Kits for Administration of Cells

These kits may also contain devices for the delivery of the cells. A variety of devices may be included depending on the targeted delivery site. Intravascular and transcutaneous delivery could be achieved with standard syringes while delivery to the brain, heart and kidney may involve specialized transluminal devices that allow for the infusion or direct injection of cells into or around the targeted organ.

3. Devices for Administration of Cells

Cells can be administered into tissue or an implant using a catheter, stent, syringe, or pump. Cells can be infused or soaked into a porous device for implantation. Cells can be suspended into a sterile solution such as phosphate buffered saline or hydrogel solution and sprayed onto a site.

II. Methods of Treatment

A. Methods of Administration

The cells can be administered to any injured tissue. Trauma, disease, chemical or other environmental exposures are other proximate causes. Ischemia is one type of condition that produces injured tissue. Preferably, B cells alone or in combination with T cells and/or phagocytic cells are administered to tissue prior to, during, or following any injury. Tissue injury may result from many different causes. For example, tissue injury may occur following ischemia, hemorrhage, trauma, surgery, inflammation, infection, burns, disease progression, aging or many other causes.

The cells may be administered directly into the injured tissue, into tissue surrounding the injury, topically, intracerebroventricularly, intramuscularly, intramyocardially, intrarenally, intrahepatically or systemically for repair of tissue and to decrease inflammation and scarring. The purpose of the cells is not to form new tissue. The use of differentiated cells insures that no undesirable differentiation occurs.

Preferably, the injections are made through a small gauge needle, preferably in the range of 32 gauge to 21 gauge, or in a range of 30 gauge to 23 gauge. The needle size may vary depending on the type, depth, and thickness of the tissue to be injected. For example in the rat, a 27 gauge needle was employed. In humans, various gauges of needles or catheters may be used. All of the procedures associated with the harvest and injection of cells are performed using sterile technique.

The cells may also be administered through a cannula placed within a body cavity, a vessel, a duct, a lumen of an organ, within an organ, a space surrounding an organ such as pericardial or pleural spaces, or intrathecally. The cells may also be applied topically for surface wounds or directly to injured tissue during surgery. In one embodiment, cells may be administered through an intraarterial cannula to injured tissue supplied by the artery.

Cells may be administered directly into the injured tissue in one or more injections. Cells may also be administered into the border zone surrounding injured tissue. In the case of infarcted cardiac tissue, cells may also be administered directly into the infarcted cardiac tissue and into the border zone surrounding the infarcted cardiac tissue. In another embodiment, cells may be administered into less than adequately perfused tissue which is not infarcted. It is to be understood that the distance or spacing between injections into the tissue will vary depending on the size of the area to receive cells and the species. For example, in rats the heart is small and the injections of cells are spaced about 1 mm to 2 mm apart.

The Boston Scientific Stiletto™ myocardial injection catheter which utilizes a 27 gauge needle may be employed. Areas of infarction are visualized using echocardiography and the injections are performed using both fluoroscopy and intracardiac echocardiographic guidance. Another technique includes the use of trans-esophageal echo. Another technique includes the use of visual, tactile and anatomical landmarks for transcutaneous direct injection. Yet another technique reported is intravenous delivery which requires no visualization technique. If intra-coronary infusion is used, fluoroscopy is the preferred method.

In one method of cell delivery, an occlusive balloon is placed proximal to the infarcted tissue to deliver cells. A common device is a PTCA balloon that is inflated using low pressure and the cells are delivered via the wire lumen. The advantage is to temporarily stop flow to enhance cell adhesion and uptake within the targeted tissue.

In another embodiment, the injections are made through vascular catheters equipped with injection means. Such catheters are guided by one of skill in the art, such as an interventional cardiologist, a veterinarian, or another trained assistant. The catheter is directed to the infarcted region through the vascular system leading to the coronary arteries using visualization techniques, including but not limited to the intracardiac echocardiography guidance (ICE) and NOGA mapping (maps electrical signal conductance) as known to one of ordinary skill in the art. NOGA is a commercial name for a catheter system that utilizes a three dimensional (3D) mapping system combined with an ECG detection algorithm that reportedly correlates the signal to myocardial viability.

In one embodiment, B and/or T cells may be administered into infarcted myocardium or into myocardium surrounding the infarcted tissue. Injection of cells into the ischemic cardiac tissue or through the cardiac vasculature enhances cardiac function following infarction to lessen the decline in or improve cardiac function following an ischemic episode. The cells may also be used to treat other conditions related to poor perfusion or less than normal blood flow and oxygenation, including, but not limited to, peripheral vascular disease, decreased tissue perfusion in diabetics for example in tissue located in the extremities, decreased cardiac perfusion in patients with atherosclerosis of one or more coronary arteries, decreased cardiac perfusion in patients undergoing bypass surgery or another cardiac procedure, renal disease including ischemic renal diseases, decreased cranial perfusion in patients with atherosclerosis of one or more carotid arteries or branches thereof, or with atherosclerosis of one or more vertebral arteries or other arteries in the cerebrovascular circulation, temporary ischemic episodes, stroke, occlusion of vessels due to trauma, a mass, or any other cause.

Based on experimental studies of B cells for treatment of ischemic cardiac tissue, 4 injections of 20 µl each, for a total of $10^6$ cells in 80 µl is injected into rat hearts weighing approximately 1.2 gm. One non-limiting range of B cell number for administration is $10^4$ to $10^{14}$ B cells, depending on the volume of infarcted tissue to be treated, and in some cases the species to be treated. Other ranges include $10^5$ to $10^{12}$ B cells and $10^6$ to $10^{10}$ B cells. For administration to larger animals higher number of cells in larger volumes may be employed. In a study performed using pig hearts, a total of $10^8$ unfractionated bone marrow cells was administered in 16 injections of 100 µl each in 1.6 ml total volume. Human patients will be treated with an effective amount of B cells which may be similar numbers of cells and similar volumes of cells as described above for use in pigs, but may be higher or lower.

Individual injection volumes can include a non-limiting range of from 1 µl to 1000 µl, 1 µl to 500 µl, 10 µl to 250 µl, or 20 µl to 150 µl. Total injection volumes per animal range from 10 µl to 10 ml depending on the species, the method of delivery and the volume of the tissue to be treated.

Methods for increasing the concentration of B cells at a desired site, such as injured tissue, can be achieved by administering a substance that binds to the B cell and also to a binding site in the vicinity of the injured tissue or to a binding site on a device located adjacent to the injured tissue. Such a substance may be a bifunctional antibody that may, for example bind to CD19 antigens on B cells and also to a binding site located in the vicinity of the injured tissue or to a binding site on a device located adjacent to the injured tissue. In this manner, the number of B cells in the vicinity of the injured tissue is increased. This method may be used whether the B cells are resident in the animal or the human, or are harvested, purified and administered to the animal or the human.

The cells to be administered are suspended in a pharmaceutically acceptable carrier such as pharmaceutically acceptable fluid. Such fluids include but are not limited to saline, cell culture medium and plasma. Additional pharmaceutically acceptable carriers include scaffolds, matrices, glues, gels and other tissue retention carriers with or without cytokines and growth factors.

B. Administration in Devices

The cells can also be administered in implants, dressings, hydrogels or medical device. For example, hydrogels, adhesives, meshes, or bandages for suturing, stapling or gluing of tissues, tissue engineering scaffolds, guided tissue repair materials, wound dressings, drug delivery vehicles, anti-adhesion barriers, cell encapsulation materials, coatings, surgical meshes, staples, and sutures may include cells.

The cells may be attached to or soaked or injected in a medical device such as implants, stents, orthopedic devices, prosthetic devices, adhesives, meniscus repair and regeneration devices, screws, bone plates and plating systems, cardiovascular patches, pericardial patches, slings, pins, articular cartilage repair devices, nerve guides, tendon and ligament repair devices, atrial septal defect patches, vein valves, bone marrow scaffolds, bone graft scaffolds, skin substitutes, dural substitutes, ocular implants, spinal fusion cages, and muscular implants (cardiac and skeletal).

A preferred fabricated form of the compositions is a porous (fibrous) construct, particularly ones which could be used as tissue engineering scaffolds, and guided tissue repair meshes and matrices. This construct or matrix may be derived by any suitable method, including salt leaching, sublimation, solvent evaporation, spray drying, foaming, processing of the materials into fibers and subsequent processing into woven or non-woven devices. Such constructs can be used in applications of the cells to the cardiovascular, gastrointestinal, kidney and genitourinary, musculoskeletal, and nervous systems, as well as those of the oral, dental, periodontal, and skin tissues. Examples of such constructs can be used to prepare scaffolds for both hard and soft tissues. Representative tissue types include, but are not limited to, cardiovascular (including blood vessel, artery, and heart valve), cornea and other ocular tissues, pancreas, alimentary tract (e.g., esophagus and intestine), ureter, bladder, skin, cartilage, dental, gingival tissue, bone, liver, kidney, genital organs (including penis, urethra, vagina, uterus, clitoris, and testis), nerve, spinal cord, meniscus, pericardium, muscle (e.g., skeletal), tendon, ligament, trachea, phalanges and small joints, fetal, and breast.

The cells may be administered in combination with or with medical devices having incorporated thereon or therein therapeutic, diagnostic or prophylactic agents. These materials may be used alone, with additives or in combinations with themselves or other materials. Additives and other materials may include those components added for the purpose of further modification of a particular property or properties, and/or those components which are biologically active such as cell attachment factors, growth factors, peptides, antibodies and their fragments.

Exemplary therapeutic agents include, but are not limited to, agents that are anti-inflammatory or immunomodulators, antiproliferative agents, agents which affect migration and extracellular matrix production, agents which affect platelet deposition or formation of thrombis, and agents that promote vascular healing and re-endothelialization, described in Tanguay et al. Current Status of Biodegradable Stents, Cardiology Clinics, 12:699-713 (1994), J. E. Sousa, P. W. Serruys and M. A. Costa, Circulation 107 (2003) 2274 (Part I), 2283 (Part II), K. J. Salu, J. M. Bosmans, H. Bult and C. J. Vrints, Acta Cardiol 59 (2004) 51.

Examples of antithrombin agents include, but are not limited to, Heparin (including low molecular heparin), R-Hirudin, Hirulog, Argatroban, Efegatran, Tick anticoagulant peptide, and Ppack.

Examples of antiproliferative agents include, but are not limited to, Paclitaxel (Taxol), QP-2, Vincristin, Methotrexat, Angiopeptin, Mitomycin, BCP 678, Antisense c-myc, ABT 578, Actinomycin-D, RestenASE, 1-Chlor-deoxyadenosin, PCNA Ribozym, and Celecoxib.

Examples of anti-restenosis agents include, but are not limited to, immunomodulators such as Sirolimus (Rapamycin), Tacrolimus, Biorest, Mizoribin, Cyclosporin, Interferon γ1b, Leflunomid, Tranilast, Corticosteroide, Mycophenolic acid and Biphosphonate.

Examples of anti-migratory agents and extracellular matrix modulators include, but are not limited to, Halofuginone, Propyl-hydroxylase-Inhibitors, C-Proteinase-Inhibitors, MMP-Inhibitors, Batimastat, Probucol.

Examples of antiplatelet agents include, but are not limited to, heparin.

Examples of wound healing agents and endothelialization promoters include vascular epithelial growth factor ("VEGF"), 1713-Estradiol, Tkase-Inhibitors, BCP 671, Statins, nitric oxide ("NO")-Donors, and endothelial progenitor cell ("EPC")-antibodies.

It may also be advantageous to incorporate in or on the device a contrast agent, radiopaque markers, or other additives to allow the device to be imaged in vivo for tracking, positioning, and other purposes. Such additives could be added to the absorbable composition used to make the device or device coating, or absorbed into, melted onto, or sprayed onto the surface of part or all of the device. Preferred additives for this purpose include silver, iodine and iodine labeled compounds, barium sulfate, gadolinium oxide, bismuth derivatives, zirconium dioxide, cadmium, tungsten, gold, tantalum, bismuth, platinum, iridium, and rhodium. These additives may be, but are not limited to, micro- or nano-sized particles or nano particles. Radio-opacity may be determined by fluoroscopy or by x-ray analysis.

Most of these materials can be sterilized by radiation sources or ethylene oxide.

C. Co-Administration of Other Therapeutic, Prophylactic or Diagnostic Agents

B cells may also be administered in conjunction with other forms of therapy. Substances which may be co-administered include but are not limited to the following: stem cell mobilizing agents (GM-CSF, SDF, GCSF, platelet-derived growth factor (PDGF)); growth factors VEGF, FGF, IGF-1; nitric oxide donors such as nitroglycerin; COX-2 inhibitors; diuretics, angiogenic factors (VEGF, angiostatin inhibitors); factors that enhance blood flow; anti-inflammatories; anti-hypertensives; HMG co-reductase inhibitors; statins; angiotensin converting enzyme (ACE) inhibitors; wound healing enhancers; NSAIDS; chemokine antagonists; thrombin; extracellular molecules; chemokines including, but not limited to, CXCL12, CXCL13, CCL19, CCL21, CCL25, CXCL9, and CXCL10; integrin ligands including but not limited to MADCAM1 (mucosal addressin cell-adhesion molecule 1) and VCAM1 (vascular cell-adhesion molecule 1); interleukin-4; and factors including any environmental cues that enhance the survival and effectiveness of the B lymphocytes or combinations thereof Agents that cause B and/or T cells to mobilize into the circulation and/or to home to the targeted tissue can also be administered, with, prior to, or after administration of the B and/or T cells, or as an alternative to administration of the cells. These methods increase levels of B and/or T cells at the targeted tissue without the need for harvest and reinjection. For example, CXCL13 is a known B cell chemokine that could be delivered to the targeted tissue along with a B cell mobilizing agent to augment presence of B cells in the targeted tissue. Another technique utilizes a chemokine antagonist that lowers the amount of chemokines contained within the targeted tissue to a level that is compatible with B cell activity. Another method is to implant a substrate or device such as an intravascular stent into or near the targeted tissue wherein the substrate or device is coated with a matrix containing an antibody which reacts with a B cell antigen thereby localizing and concentrating B cells at the implant site. In this method, the number of circulating B cells could be augmented through the harvest from another organ such as bone marrow, isolated, concentrated and delivered back to the patient's blood system.

Other methods to condition B or T cells in vivo to promote adherence of the B cell to the surface of the implanted substrate, device or injured tissue in order to concentrate or increase their levels at the targeted tissue can be employed. In this technique, a substance could be delivered systemically, such as a bifunctional antibody, that adheres to surface antigens on the cells, for example the CD19 surface antigen for B cells, and also adheres to the implant surface or injured tissue to cause B cell localization at that site. This approach can be used in conjunction with administration of autologous B and/or T cells harvested from the animal or human. This approach can also be used in situations wherein autologous cells are not harvested from the animal or human but when an increase of endogenous cells at the injured tissue is desired. For example, administration of such a substance to the animal or the human with the injured tissue can bind to available B cells, such as circulating B cells, and also to the site of the injured tissue, thereby increasing the number of B cells at the site.

III. Kits

Kits are provided for use in isolation and for administration of the isolated cells. Kits may employ positive selection techniques, negative selection techniques, or a combination thereof, to isolate a relatively pure population of B and/or T cells from a heterogeneous mixture of cells. Positive selection techniques employ antibodies that recognize antigens on the B and/or T cells. Antibodies that recognize antigens B cells include, but are not limited to, antibodies that bind CD19, CD19+, B220+ or B cell receptor (Ig.alpha.beta.)+.

Negative selection techniques employ antibodies that include, but are not limited to, antibodies that bind the following human cell surface antigens: CD2, CD3, CD14, CD16, CD36, CD43, CD56, and glycophorin A that reside on T cells, NK cells granulocytes, monocytes/macrophages, and erythrocytes.

Generally speaking, kits include a separation chamber, optionally including: a centrifugation chamber; a collection bag connected to the separation chamber; means to connect the collection bad to the separation chamber such as connection units, connection lines, and luers; a manifold, antibodies that recognize antigens on B cells or antibodies that recognize antigens on non B cells, or both; separation means such as a filter or a column; and, a collection vial for the isolated B cells.

Antibodies may optionally be linked to magnetic beads as known to one of ordinary skill in the art. Kits may employ affinity columns in which antibodies used for positive or negative selection are suspended in a medium such as a chromatography medium known to one of ordinary skill in the art, for example Sepharose. Such antibodies have been described elsewhere in this application. Such affinity columns may act as separation chambers. Another separation chamber is a tube coated with antibodies on its inner wall.

Kits may also employ materials such as polystyrene, polypropylene, stainless steel, nitinol, rubber or other materials known to bind to cells.

Kits optionally contain buffers for elution of bound cells or cells trapped by a filter, a buffer for resuspending the isolated B cells before administration to the human. Filters that trap cells and separate cells from viruses or other undesired plasma components may also be employed.

Kits may also include devices and means for administration to the patient.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

We claim:

1. A method of enhancing normal healing in individuals comprising administering to a site in need thereof an effective amount of a composition comprising autologous isolated B cells in a pharmaceutically acceptable carrier immediately before, at the time of or immediately after tissue injury, wherein the autologous isolated B cells are prepared by a method comprising substantially removing stem cells from a heterogeneous population of cells containing the stem cells and the autologous B cells to isolate the B cells.

2. The method of claim 1 wherein the injured tissue is cardiac tissue damaged by ischemia.

3. The method of claim 1 wherein the injured tissue is prone to scarring, and the B cells limit overproliferation of tissue.

4. The method of claim 1 wherein the tissue has been excised to remove cancerous or infected tissue, wherein the isolated B cells limit metastasis or spread of infection.

5. The method of claim 1 wherein the isolated B cells are administered prior to, during or after placement of an implant.

6. The method of claim 1 wherein the isolated B cells are administered prior to, during or after surgery to the tissue.

7. The method of claim 1 wherein the isolated B cells are administered using a syringe, stent, catheter or infusion pump.

8. The method of claim 1 wherein the isolated B cells are administered attached to or within an implant, wound dressing, hydrogel, or medical device.

9. The method of claim 1 wherein the isolated B cells are cells exhibiting at least one surface protein selected from the group consisting of B220, CD19, CD5, IgM, IgD, IgG, CD23, CD21, CD40 and B cell receptor ($Ig_{\alpha\beta}$).

10. The method of claim 1 wherein the isolated B cells are all terminally differentiated.

11. The method of claim 1 wherein the isolated B cells are administered locally.

12. The method of claim 1 wherein the isolated B cells are administered systemically.

13. The method of claim 1 wherein the isolated B cells are primed by initially culturing under anoxic conditions, using biological or chemical inducers, or by exposure to varying chemical or physical conditions including temperature, pressure, osmotic conditions, pH, or varying concentrations of molecular compounds or electrolytes.

* * * * *